· US011259694B2

(12) United States Patent
Mach

(10) Patent No.: US 11,259,694 B2
(45) Date of Patent: Mar. 1, 2022

(54) WINDOW ASSEMBLY FOR ENDOSCOPIC PROBE

(71) Applicant: Canon U.S.A., Inc., Melville, NY (US)

(72) Inventor: Anderson Thi Mach, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 52 days.

(21) Appl. No.: 16/746,154

(22) Filed: Jan. 17, 2020

(65) Prior Publication Data

US 2020/0245854 A1   Aug. 6, 2020

Related U.S. Application Data

(60) Provisional application No. 62/799,146, filed on Jan. 31, 2019.

(51) Int. Cl.
*A61B 1/07* (2006.01)
*A61B 1/00* (2006.01)

(52) U.S. Cl.
CPC .............. *A61B 1/07* (2013.01); *A61B 1/0011* (2013.01); *A61B 1/00073* (2013.01); *A61B 1/00096* (2013.01)

(58) Field of Classification Search
CPC ..... A61B 1/00096; A61B 1/0011; A61B 1/07; A61B 8/12; A61B 1/127; A61B 1/128
(Continued)

(56) References Cited

U.S. PATENT DOCUMENTS 3,224,916 A   12/1965 Soloff et al.
3,563,822 A   2/1971 Fesh
(Continued)

FOREIGN PATENT DOCUMENTS

JP   S58184922 A   10/1983
JP   05-329156 A   12/1993
(Continued)

OTHER PUBLICATIONS

Lee, C. M., et al., "Scanning fiber endoscopy with highly flexible, 1mm catheterscopes for wide-field, full-color imaging", J Biophotonics, Jun. 2010, pp. 385-407, vol. 3, No. 5-6.

*Primary Examiner* — Michael J Carey
*Assistant Examiner* — Stephen Floyd London
(74) *Attorney, Agent, or Firm* — Canon U.S.A., Inc., IP Division

(57) ABSTRACT

Endoscope window assembly designs and methods of assembling sub-millimeter imaging endoscopes are disclosed. An endoscope apparatus comprises an elongated cylindrical probe having rotating illumination optics in the middle and at least one detection fiber and a spectrometer connected to the detection fiber and a light source connected to the illumination optics and a processor for imaging. An optically transparent window is attached to the cylindrical probe at the distal end thereof, the window seals the rotating illumination optics inside the cylindrical probe, and the at least one detection fiber is located on the outer surface of the cylindrical probe. The present disclosure provides various embodiments of a window component that covers only the illumination component of the optical probe. Endoscope embodiments where the window component covers only the illumination component eliminate or significantly reduce exposure of detection fibers to reflected illumination light without blocking a light collection optical path.

15 Claims, 9 Drawing Sheets

(58) Field of Classification Search
USPC .................................................. 600/137, 140
See application file for complete search history.

(56) References Cited

U.S. PATENT DOCUMENTS

| | | | | |
|---|---|---|---|---|
| 3,998,216 A | * | 12/1976 | Hosono | A61B 1/0055 |
| | | | | 600/140 |
| 4,176,662 A | * | 12/1979 | Frazer | A61B 1/00156 |
| | | | | 138/103 |
| 4,790,295 A | | 12/1988 | Tashiro | |
| 4,869,238 A | * | 9/1989 | Opie | A61B 1/00071 |
| | | | | 600/109 |
| 5,108,411 A | | 4/1992 | McKenzie | |
| 5,337,734 A | * | 8/1994 | Saab | A61B 1/00142 |
| | | | | 600/121 |
| 5,347,990 A | | 9/1994 | Ebling et al. | |
| 5,536,244 A | | 7/1996 | Muller et al. | |
| 5,538,497 A | | 7/1996 | Hori | |
| 6,863,651 B2 | | 3/2005 | Remijan et al. | |
| 8,679,002 B2 | | 3/2014 | Sutoh et al. | |
| 9,477,075 B2 | | 10/2016 | Kiedrowski | |
| 9,801,525 B2 | | 10/2017 | Eisenkolb et al. | |
| 9,888,834 B2 | | 2/2018 | Buerk et al. | |
| 10,337,987 B2 | | 7/2019 | Wu et al. | |
| 2005/0283048 A1 | | 12/2005 | Gill et al. | |
| 2010/0217080 A1 | | 8/2010 | Cheung et al. | |
| 2010/0249601 A1 | * | 9/2010 | Courtney | A61B 5/6852 |
| | | | | 600/463 |
| 2011/0237892 A1 | * | 9/2011 | Tearney | A61B 5/0084 |
| | | | | 600/160 |
| 2012/0101374 A1 | * | 4/2012 | Tearney | G01N 21/6456 |
| | | | | 600/427 |
| 2012/0230636 A1 | * | 9/2012 | Blockley | G02B 6/4477 |
| | | | | 385/59 |
| 2012/0253130 A1 | | 10/2012 | Motoyama | |
| 2014/0152789 A1 | * | 6/2014 | Hu | G02B 6/449 |
| | | | | 348/65 |
| 2017/0261742 A1 | * | 9/2017 | Wieters | A61B 1/0008 |
| 2017/0290492 A1 | * | 10/2017 | Hamm | A61B 1/00165 |
| 2017/0360398 A1 | | 12/2017 | Hamm et al. | |
| 2018/0125372 A1 | * | 5/2018 | Petroff | G02B 6/3604 |
| 2019/0200867 A1 | * | 7/2019 | Yokota | G02B 26/103 |

FOREIGN PATENT DOCUMENTS

| | | | | |
|---|---|---|---|---|
| JP | 2004-329235 A | | 11/2004 | |
| JP | 2011-209425 A | | 10/2011 | |
| JP | 2017-505667 A | | 2/2017 | |
| JP | 2017-202140 A | | 11/2017 | |
| WO | 82/02604 A1 | | 8/1982 | |
| WO | 97/34175 A1 | | 3/1997 | |
| WO | 97/34175 A1 | | 9/1997 | |
| WO | WO-2014158140 A1 | * | 10/2014 | ........... A61B 1/0607 |
| WO | 2016040131 A1 | | 3/2016 | |

* cited by examiner

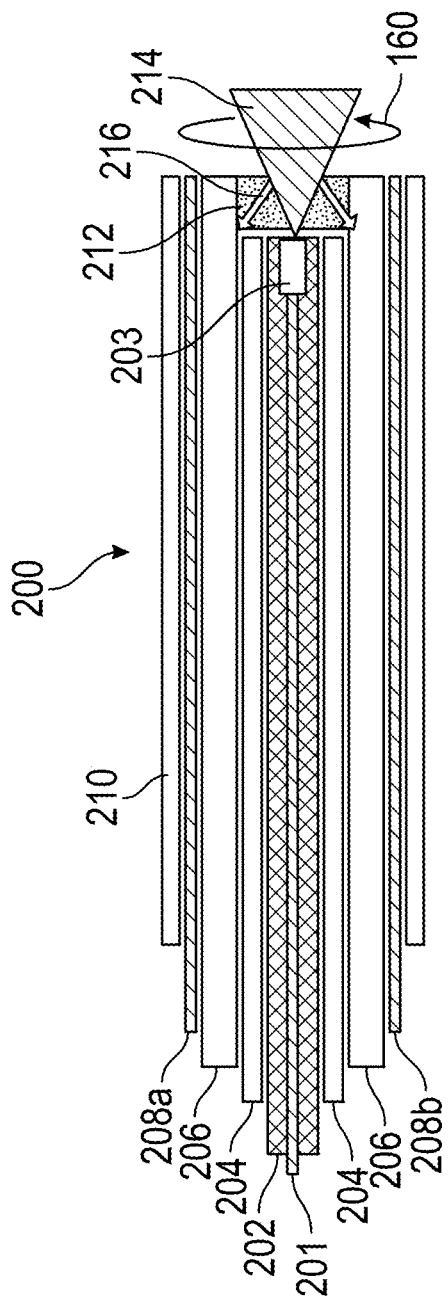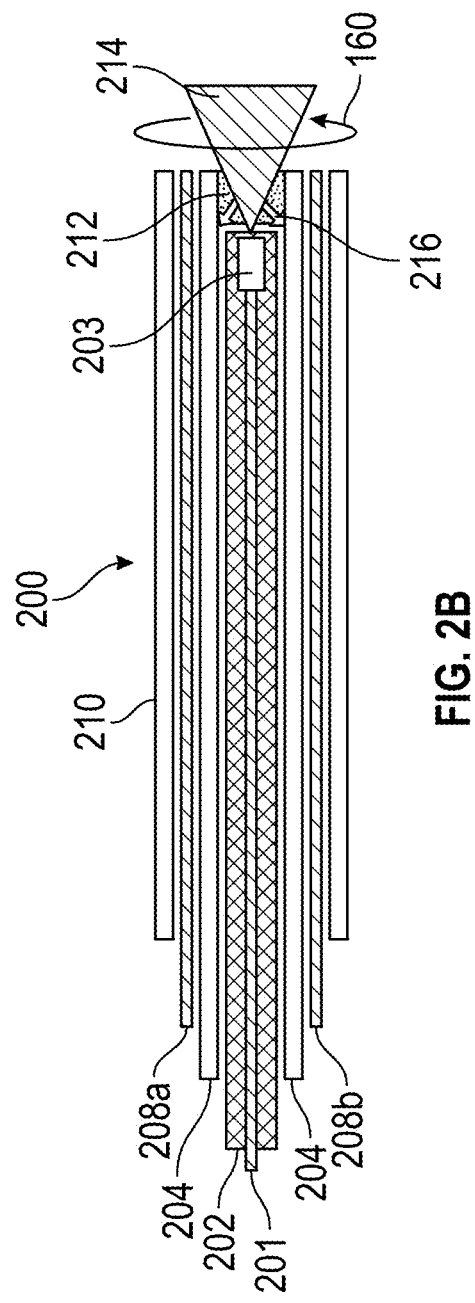

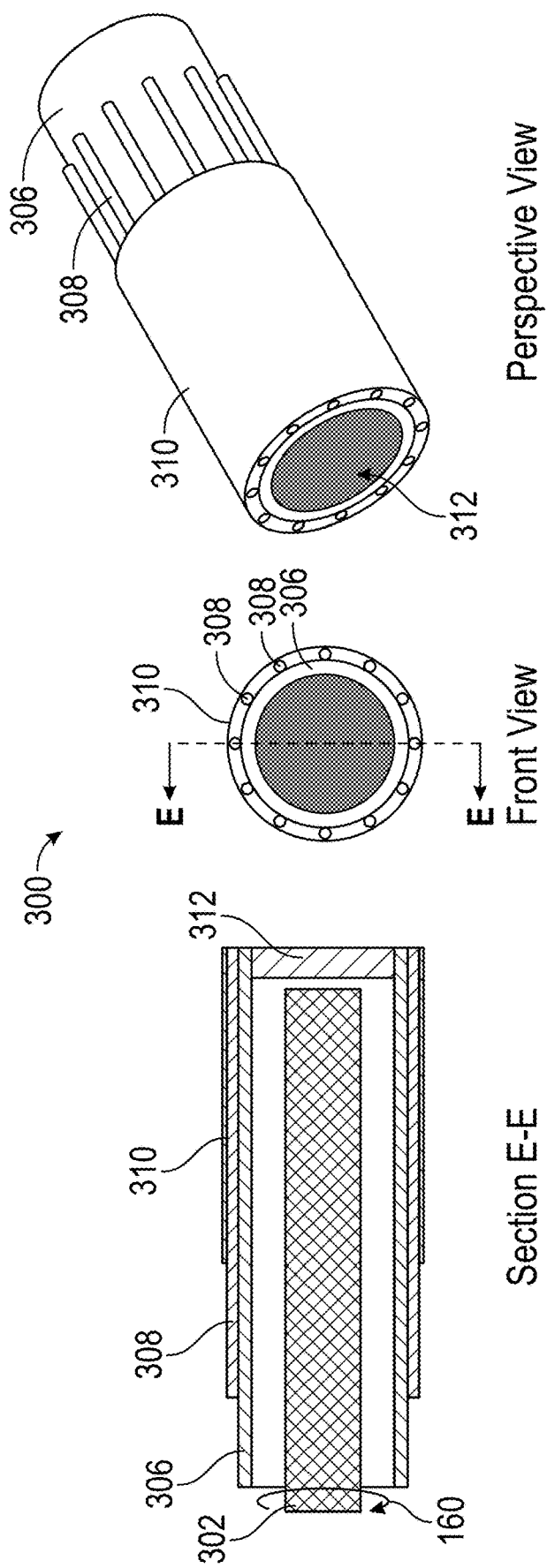

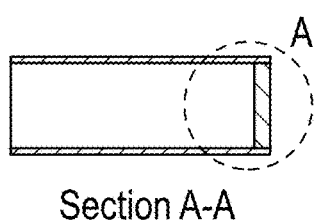 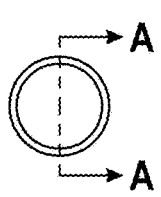 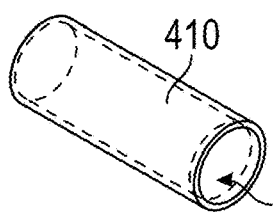 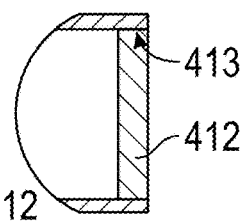
Section A-A     FIG. 4A     Detail A
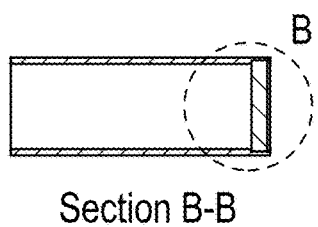 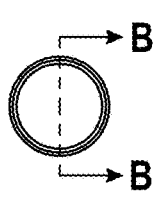 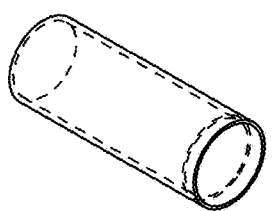 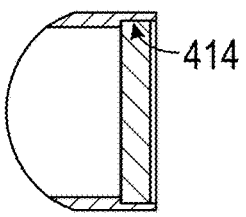
Section B-B     FIG. 4B     Detail B
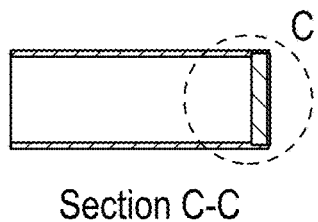 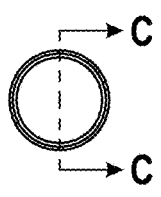 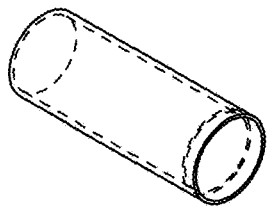 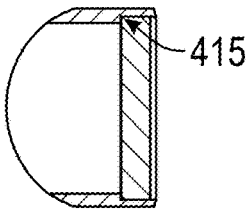
Section C-C     FIG. 4C     Detail C
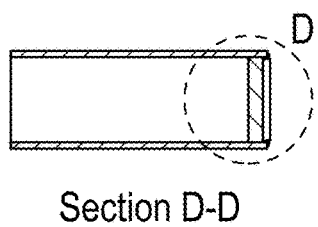 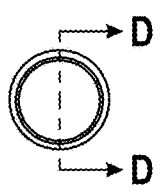 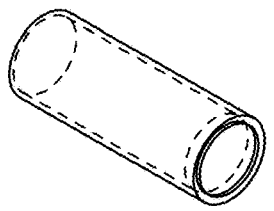 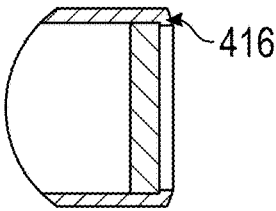
Section D-D     FIG. 4D     Detail D
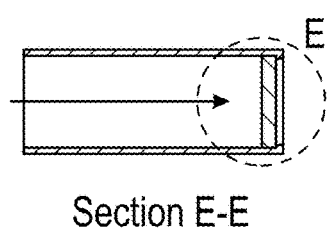 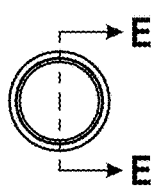 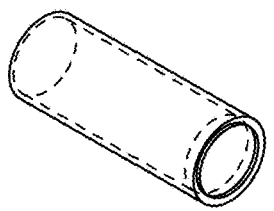 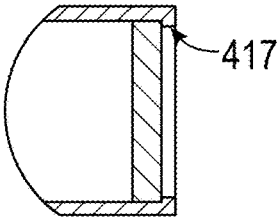
Section E-E     FIG. 4E     Detail E

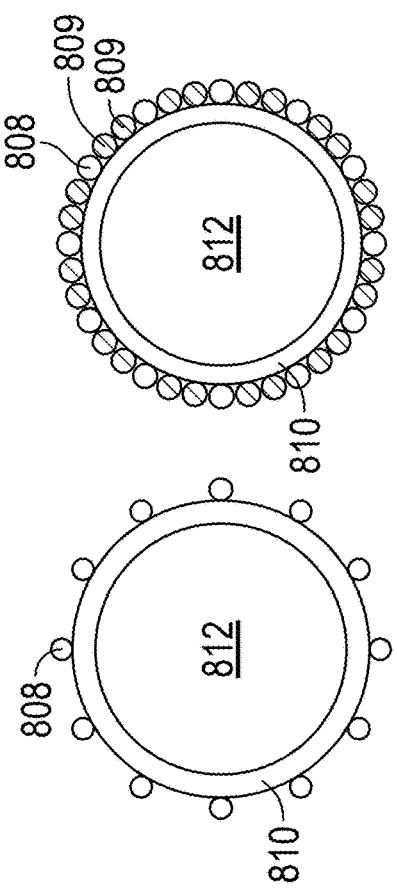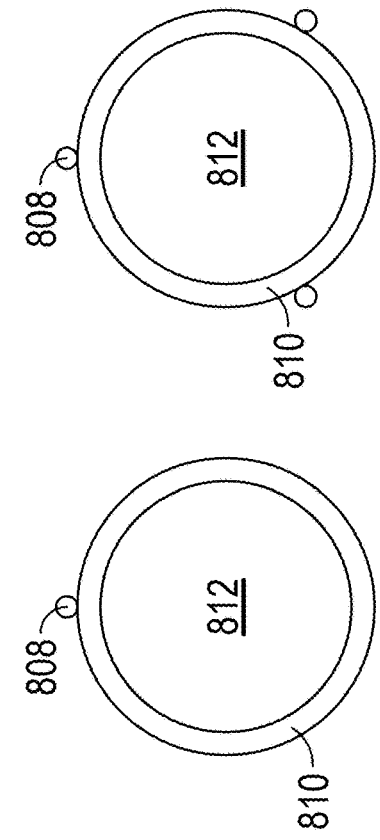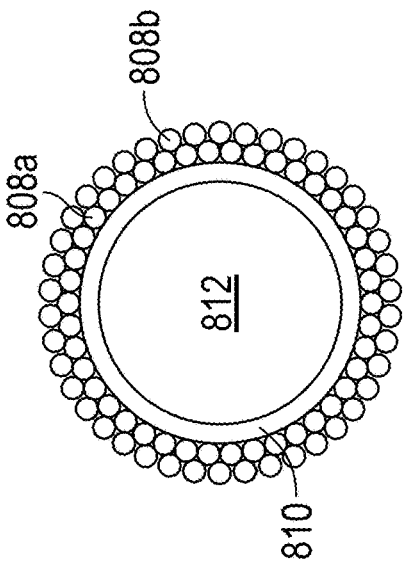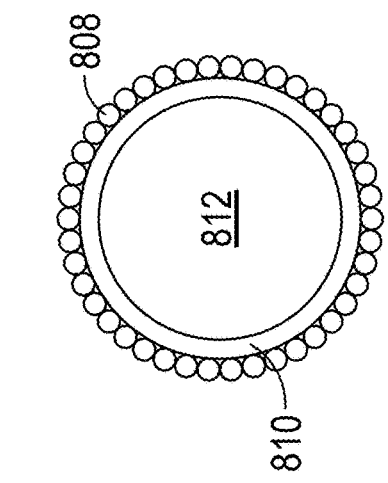

WINDOW ASSEMBLY FOR ENDOSCOPIC PROBE

CROSS-REFERENCE TO RELATED APPLICATIONS

The present application claims priority to U.S. provisional application 62/799,146, filed Jan. 31, 2019, the disclosure of which is incorporated by reference herein in its entirety.

BACKGROUND INFORMATION

Field of the Disclosure

The present disclosure generally relates to medical imaging devices. More particularly, the disclosure exemplifies endoscope window assembly designs, and methods for fabricating sub-millimeter medical imaging endoscopes.

Description of Related Art

Medical imaging devices such as endoscopes require an illumination component and a detection component. For endoscopes designed for in-vivo use, a window component is needed to protect the core optics from contamination from outside elements such as dust, liquids, or bodily fluids which will degrade image quality. The window component is made of medical grade transparent material (e.g., glass or plastic) which allows for light to be output for illumination and collected for detection with minimum transmission losses. The window is typically assembled in the distal end of a metallic or plastic tube (sheath) which is used to cover the endoscope core optics. For example, U.S. Pat. No. 5,347,990 describes an endoscopy probe having a fiber optic image bundle that can be encased in a sterile sleeve with a window at the distal end of the sleeve. Similarly, U.S. Pat. No. 8,679,002 describes an endoscopy probe having a fiber optic and a protective cover with a light-transmissive widow at the distal end thereof. Further, U.S. Pat. No. 5,337,734 describes an endoscopy probe with a sterile cover/sheath with an optically transparent window and also provides a method of making such sheath.

In most endoscopes, the illumination component includes an optical probe having an optical fiber and distal optics at the distal end of the fiber, which are rotated or oscillated together to output light to scan a region of a sample to be imaged. The illumination fiber and distal optics are assembled inside a hollow drive shaft (drive cable) connected to a motor, such that the drive shaft transmits rotational torque from the motor to the distal end of the probe. The drive shaft may be a rigid tube or flexible torque wire or drive cable. The illumination core (drive shaft containing the optical probe) rotates within a sheath which has a low-friction inner surface. The detection component often includes a plurality of stationary fibers fixed to the outer surface of sheath. These fibers (referred to as "detection fibers") are arranged surrounding the distal end of the sheath.

For endoscopes with an outer diameter (OD) of 2 millimeters (mm) or less, assembly methods and material selection are very important to keep the cost of the endoscope low and the footprint of the window component as small as possible. In a spectrally encoded endoscope (SEE) with forward-viewing capability, the detection component comprises one or more fibers that collect the light reflected from a sample and carry the collected light from the distal end of the endoscope to a detector and/or a spectrometer, so that detected signals can be processed by a computer. The SEE endoscope, to be used for in-vivo examination of delicate bodily lumen, is preferably a sub-millimeter endoscope (i.e., an endoscope with OD<1 mm). Therefore, the window is a critical component of the SEE endoscope. In particular, the window allows passage of light for illumination and for detection, and acts as the protective barrier between the inner endoscope components and the outside elements (bodily fluids, blood, tissue, etc.) of a patient's body.

Due to the reduced size requirements for the window component, the choice of material, the design parameters, and the assembly process have proven to be very challenging in achieving the aforementioned requirements to keep the cost of the endoscope low and the footprint of the window component as small as possible. More specifically, as mentioned above, the window fixed to the distal end of the probe not only increases the size and weight of the probe, but it also adds difficulty to the assembly process, and may provide the potential for device failure due to the manner in which the window is conventionally attached to the probe.

Specifically, window fixation must prevent leakage of fluids into the endoscope optics (illumination and detection component), while still maintaining the cost and time of assembling low. To that end, it is important to encounter a careful balance between keeping costs low and achieving effective window fixation and hermetic sealing processes. In conventional systems, epoxy is typically used for window fixation. However, although epoxy bonds well with endoscope materials such as polytetrafluoroethylene (PTFE), polyimide (PI), or similar low-friction surface materials, the bond is not secure because PTFE and similar materials do not resist high mechanical stress or pressure. Epoxy bonds in metal tubes are stronger than in plastic tubes, but it adds significant size to the overall endoscope outer diameter (OD). Another issue is the need for stability during probe rotation. Due to high-speed rotation, the window could dislodge and pop out if the bond is broken. Detection fibers assembled on the outer surface of the inner sheath are prone to slippage or detachment from the inner sheath due to the low-quality bonding between the fibers and the outer surface of the sheath. For scopes that have a window that covers both illumination and detection components, the illumination light can reflect back off of the surface of the window and enter the detection fibers thereby negatively affecting image quality.

The adhesive bond strength between a sheath of low-surface energy properties and fibers is very weak and prone to result in fiber dislodgement from the sheath surface during endoscope bending and/or stretching. Moreover, for endoscopes that have a window that covers both illumination and detection fibers, the illumination light can reflect back off of the surfaces of the window and enter the detection fibers thereby negatively affecting image quality.

SUMMARY OF EXEMPLARY EMBODIMENTS

According to at least one embodiment, the present disclosure provides describes endoscope window assembly designs and methods of fabricating sub-millimeter medical imaging endoscopes which overcome at least some of the issues discussed in the background section above. According to one aspect of the present disclosure, an endoscope apparatus comprises an elongated cylindrical probe having rotating illumination optics in the middle and at least one detection fiber and a spectrometer connected to the detection fiber and a light source connected to the illumination optics and a processor for imaging. An optically transparent window is attached to the cylindrical probe at the distal end thereof, the window seals the rotating illumination optics inside the cylindrical probe, and the at least one detection fiber is located on the outer surface of the cylindrical probe. Advantageously, the window is designed to only cover the illumination optics of the scope, thereby preventing the detection optics from being exposed to reflected illumination light.

The cylindrical probe is processed as a thru-cylinder, slotted, bored from the proximal end, or rolled, for attaching the window thereto. In one embodiment, the cylindrical probe has grooves on the outer surface thereof; the grooves extend parallel to the length direction of the probe and serve for arranging therein detection fibers with accurate alignment and even distribution around the outer surface.

In one embodiment, the cylindrical probe includes a flexible sheath housing the rotating illumination optics thereinside, and the sheath includes a metal coil embedded within the wall of the sheath. In at least one embodiment, the window is circular piece of glass coated with anti-reflective coating material or with reflection suppressing/reducing coating material.

In at least one embodiment, the window is a cored window of slide glass and fitted to the inner diameter of the cylindrical probe. In at least one embodiment, the window is a glass-rod window made of a single glass-rod fitted to the inner diameter of the cylindrical probe, and then polished after attaching to the cylindrical probe.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 2A and FIG. 2B illustrate an exemplary embodiment of a window assembly 200 for a forward-viewing endoscope according to the present disclosure.

FIG. 3A and FIG. 3B show exemplary arrangements of a window and illumination fibers arranged at the distal end of the endoscope, according to the present disclosure.

FIGS. 4A, 4B, 4C, 4D, 4E show various exemplary designs of a metallic cylinder configured to assemble therein a transparent window at the distal end thereof.

FIGS. 8A, 8B, 8C, 8D, 8E, 8F show various examples of the manner in which detecting fibers can be arranged concentrically around the distal end of a cylindrical tube or inner sheath.

DETAILED DESCRIPTION OF EXEMPLARY EMBODIMENTS

Figure 1A:
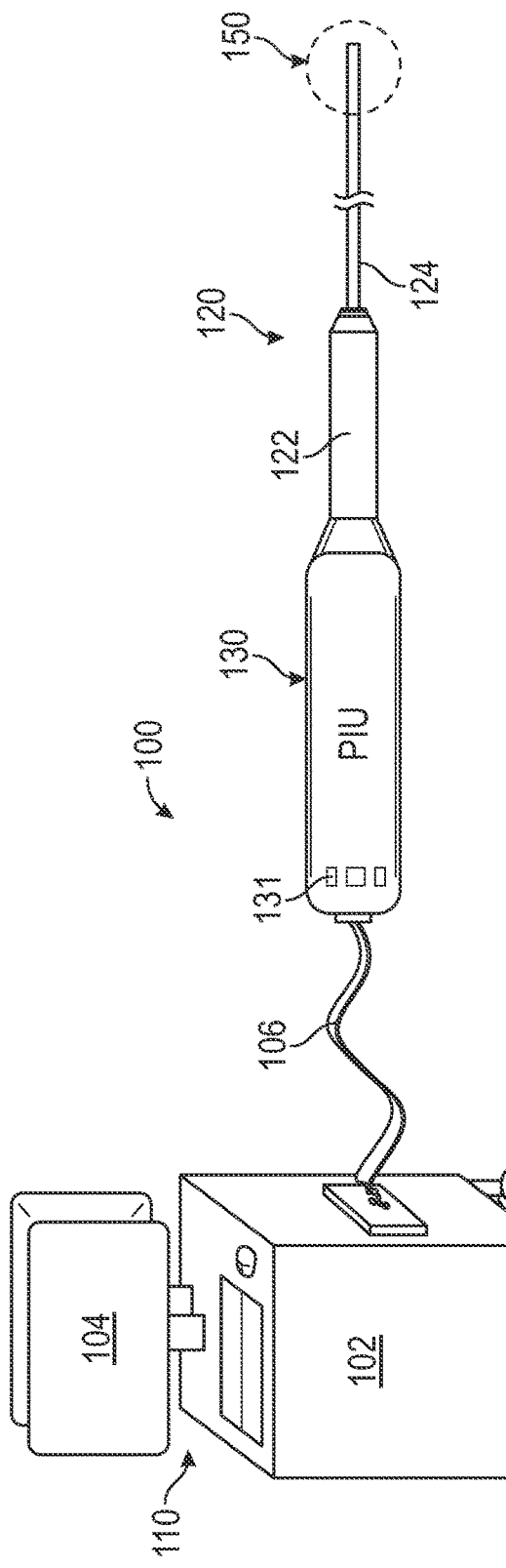
FIG. 1A illustrates an exemplary imaging system in which the endoscopic window assembly of the present disclosure may be practiced.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

The embodiments are based on the object of providing an endoscope window component of sub-millimeter outer diameter (OD) and thickness as small as possible. In one embodiment, the thickness of the window is in the range of about 100-200 micrometers ($\mu m$). To facilitate assembly and handling, the window material preferably has high optical quality and the window is arranged substantially parallel to the distal optics. To ensure durability and stability, fixation of the window to the distal end of the probe must be hermetic, strong, yet light (low weight).

Although endoscopic window concepts have been already described by the applicant of the instant application (see, e.g., US 2017/0290492, US 2017/0360398), the present disclosure is a novel improvement in the previously disclosed concepts. A difference between the present disclosure and the previously disclosed window concept is that in the present disclosure the inner tube for a SEE endoscope houses a rotating element and thus the inner tube is of a lubricious material which is not easily bondable. A ring of fibers is used for light detection (in some embodiments the ring of fibers may be used for illumination). For a SEE endoscope, according to the present disclosure, the disposable scope is comprised of the detection sheath and the rotating illumination probe. The detection sheath is the assembly of the ring of detection fibers, the inner tube, and the window. The illumination probe is assembled within the inner tube. The disposable scope is connected, at the distal end thereof, to a multi-use handle which houses the motor that drives the illumination probe rotation. In the present disclosure, the window and fiber ring assembly is part of the disposable sheath that goes over the non-disposable detection sheath. The present disclosure describes the design and assembly of fixing a transparent window component to other elements (fibers, drive cable, embedded tubes) at the distal end of the endoscope.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

<Imaging System>

Figure 1B:
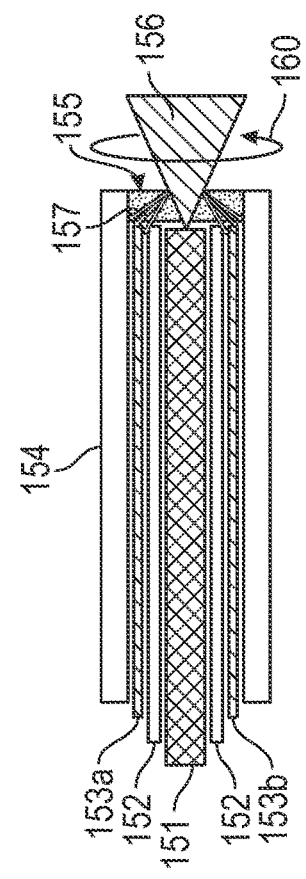
FIG. 1B illustrates a known endoscope window assembly where reflected illumination light disadvantageously reaches the detection fibers.

FIG. 1A illustrates an exemplary imaging system in which the endoscopic window assembly of the present disclosure may be practiced. FIG. 1B illustrates endoscope window assembly where reflected illumination light may reach the detection fibers. More specifically, FIG. 1A shows an exemplary medical imaging system 100 on which the invention of the present disclosure can be practiced. The medical imaging system 100 includes an imaging console 110 and an optical probe 120 (e.g., a SEE endoscope). A patient interface unit (PIU) 130 connects the optical probe 120 to the imaging console 110 using a cable bundle 106. The imaging console 110 includes, among other things, a computer cart 102 and one or more displays 104. The optical probe 120 may include, for example, a fiber-optic based endoscope 124, and an endoscope handle 122. The endoscope handle 122 removably engages with the PIU 130 on one end and with the endoscope 124 on the opposite end. The endoscope 124 includes at its distal end thereof a distal optics assembly 150 which includes illumination optics to illuminate a sample with light, and detection optics to collect light (reflected, scattered, and/or emitted) from the sample.

The PIU 130 is the main interface between the endoscope and the console 110. The PIU 130 provides the means to spin and linearly translate the imaging optical core within the scope's stationary outer sheath. The console 110 and PIU 130 are connected by the PIU cable bundle 106. The cable bundle 106 includes therein cables for transmitting electrical power and for communication signaling, as well as optical fibers for illumination and collection of light. During operation of the imaging system 100, the PIU 130 is preferably covered with a sterile drape and placed on the patient's bed or operating table. The PIU 130 may provide a user interface for operating the imaging functions of the probe from a sterile field by the use of actionable buttons 131; these buttons 131 may mirror other controls provided on a graphical user interface (GUI) in display 104 at the imaging console 110. The state of each button 131 (e.g., active, inactive, warning, etc.) is communicated by indicator LEDs provided on the housing of the PIU 130; and these indicators too are mirrored on the GUI of display 104. Therefore, users of the medical imaging system 100 may perform the same operations from either a non-sterile filed using the GUI in display 104 or from the sterile field using the buttons 131 of the PIU 130. The PIU 130 may include, among other things, a non-illustrated fiber optic rotary joint (FORJ) composed of a beam combiner, a motion mechanism including a rotational motor to rotate or oscillate illumination optics arranged inside the optical probe 120 in rotational direction 160.

The medical imaging system 100 can operate a spectrally encode endoscope (SEE) probe, consisting of rotating illumination optics arranged inside the probe, and at least one detection fiber arranged on the outer surface of the probe. The console 110 may include a spectrometer connected to the at least one detection fiber, and a light source connected to the illumination optics, and as well as a processor cooperating with the light source and spectrometer for imaging a sample or subject (not shown).

FIG. 1B shows in more detail the distal optics assembly 150 of the optical probe 120, according to one embodiment. As shown, the distal optics assembly may include a window 155 configured to hermetically seal inside a metallic cylinder 154 an imaging core composed of a plurality of optical fibers and miniature optics as known in the art.

More specifically, in FIG. 1B, the distal optics assembly includes an imaging core 151 which includes a first fiber and distal optics (not shown) enclosed in a rotatable drive cable, an inner sheath 152, second fibers 153a and 153b surrounding the imaging core 151, a protective metallic cylinder (metal can) 154, and a transparent window 155. At the distal end of the imaging core 151, the first fiber and distal optics thereinside may emit (or collect) a light beam 156. In the case where the imaging core 151 is configured to guide illumination light, the light beam 156 transmits through the window 155, and part of the light is reflected by the surfaces of window 155 as reflected light 157. The reflected light 157 returns towards the second fibers 153a and 153b. In this case, the second fibers 153a and 153b will collect the reflected light 157 and will also collect light (reflected, scattered, and/or emitted) from the sample. Alternatively, the imaging core 151 may be configured to collect light from the sample, and the second fibers 153a and 153b can be configured as illumination fibers. In the case that the second fibers are illumination fibers, at least one of second fibers 153a and 153b guides illumination light to be transmitted through window 155, and part of the light will be partially reflected by the surfaces of the window 155 and collected by the imaging core 151 as part of the light beam 156. As will be understood by those of ordinary skill in the art, the collection of reflected light 157 together with light (reflected, scattered, and/or emitted) from the sample may be undesirable.

FIG. 2A and FIG. 2B illustrate another embodiment of a window assembly 200 for a forward-viewing endoscope according to the present disclosure. As explained above, known endoscopes incorporate a window design that covers both illumination and detection optical elements. In such configuration, the detection fibers are exposed to reflected light from the window surfaces, thereby creating imaging distortion. In contrast, the present disclosure provides various embodiments of a window component that optically separates the light collection component from the illumination component of the optical probe. Advantageously, endoscope embodiments where the window component covers and seals only the illumination component (or only the light collecting component) inside the metal can or inner sheath eliminate or significantly reduce the amount of reflected light exposure to the detection fibers.

<Window Assembly Designs>

FIG. 2A shows a first embodiment of an exemplary window assembly 200, according to the present disclosure. As shown in FIG. 2A, an endoscope includes concentrically arranged a rotatable drive cable 202, an inner sheath 204, a protective metal can 206, and a protective outer sheath 210. A first optical fiber 201 and distal optics 203 (including a GRIN lens, a spacer, and a grating and/or a prism or mirror) are arranged within the drive cable 202. A plurality of second optical fibers 208a and 208b are arranged between the metal can 206 and the protective outer sheath 210. An optical window 212 is arranged at the distal ends of the drive cable 202 and inner sheath 204. From the distal end of drive cable 202, the first optical fiber 201 and distal optics 203 therein side either guide a light beam 214 towards an imaging plane or collect light (reflected, scattered and/or emitted) from the sample located at the imaging plane. In either case, the light beam 214 transmits through the optical window 212 while the drive cable 202 rotates in a rotational direction 160.

In the present embodiment, the protective metal can 206 holds thereinside at the distal end thereof the window 212 such that the distal end of the metal can 206 is flush with the front surface (distal surface) of the window 212, and the second optical fibers 208a and 208b are arranged on the outer surface of the protective metal can 206. The distal ends of second optical fibers 208a and 208b are also flush with the distal end of metal can 206 and with the front surface (distal surface) of window 212. With this arrangement, the window 212 sits in the optical path of the light beam 214 without interfering with the optical path of the second optical fibers 208a and 208b.

In some embodiments as described by FIG. 2A, the second optical fibers 208a and 208b are referred to as detection fibers 208a and 208b, and these fibers are enclosed by the protective outer sheath 210. When the second optical fibers 208a and 208b are configured as detection fibers 208a and 208b, the first optical fiber 201 is referred to as illumination fiber 201 and together with the distal optics 203 are configured as an illumination component which guides illumination light towards a sample.

Specifically, from the distal end of the rotatable drive cable 202, the illumination fiber 201 and distal optics 203 thereinside guide a light beam 214 towards a sample located an imaging plane (or working distance). The light beam 214 (illumination light) transmits through the optical window 212, and at least part of the illumination light is reflected by the surfaces of window 212 as reflected light 216. In the present embodiment, the protective metal can 206 holds thereinside at the distal end thereof the window 212 such that the distal end of the metal can 206 is flush with the front surface (distal surface) of the window 212, and the detection fibers 208a and 208b are arranged on the outer surface of the protective metal can 206. The distal ends of detection fibers 208a and 208b are also flush with the distal end of metal can 206 and with the front surface (distal surface) of window 212. With this arrangement, the window 212 sits in the optical path of the illumination light (light beam 214) without interfering with the light collection optical path of the detection fibers 208a and 208b. That is, by arranging the distal surface of window 212 flush with the distal end of the metal can 206 and flush with the distal ends of detection fibers 208a and 208b, the collection optical path between the detection fibers and the imaging plane (sample) is not interfered. Therefore, the reflected light 216 reflected by the surfaces of window 212 is confined to the inside of the metal can 206 and cannot advance towards the detection fibers 208a and 208b. In other words, the metal can 206 prevents reflection light from reaching the detection fibers because the illumination light reflected from the surfaces of window 212 does not reach the distal ends of detection fibers 208a and 208b.

In an alternative arrangement of the embodiment shown in FIG. 2A, an endoscope includes concentrically arranged a drive cable 202, an inner sheath 204, a protective metal can 206, one or more illumination fiber(s) 208a and/or 208b, and a protective outer sheath 210. A transparent imaging window 212 is arranged at the distal ends of the drive cable 202 and inner sheath 204. The drive cable 202 includes thereinside at least a detection fiber or fiber bundle 201 and distal optics 203 (including, e.g., a lens, a spacer, and a grating and/or a prism or mirror). From the distal end of drive cable 202, the detection fiber 201 and distal optics 203 thereinside collect light (reflected, scattered, and/or emitted) from the sample and transmitted through the window 212. In this alternative arrangement of the present embodiment, the protective metal can 206 holds thereinside at the distal end thereof the window 212 such that the distal end of the metal can 206 is flush with the front surface (distal surface) of the window 212, and the illumination fiber(s) 208a and/or 208b as well as other fibers that may be used, for example, for therapy light, are arranged on the outer surface of the protective metal can 206, and configured to at least partially surround the distal end of the metal can 206. The distal ends of these illumination fibers 208a and 208b are also flush with the distal end of metal can 206 and with the front surface (distal surface) of window 212. With this arrangement, the window 212 sits in the optical path of the light beam 214 (light reflected, scattered, and/or emitted from the sample) entering the detection optics without interference from the illumination fibers 208a and/or 208b. Therefore, illumination light exiting the distal ends of illumination fibers 208a and/or 208b will not be reflecting off the window 212 and will not advance into the detection fiber 201 since the surfaces of window 212 are confined to the inside of the metal can 206 and cannot receive light reflected from a position flush with the window. Thus, the illumination light leaving the illumination fiber(s) 208a and/or 208b does not reach the detection fiber 201 and distal optics 203. As illustrated in FIG. 2A, the drive cable 202 is configured to rotate the first fiber 201 and distal optics 203 with respect to the inner sheath 204. However, in a further modification, second fibers 208a and 208b can also be configured to rotate in direction 160 with respect to the inner sheath 204. Examples where the illumination optics and/or the detection optics are configured to rotate with respect to the probe axis can be found in the applicant's previous U.S. Pat. No. 10,337,987, which is hereby incorporated by reference. These alternative modifications to the embodiment of FIG. 2A also apply to the embodiment of FIG. 2B described below.

FIG. 2B shows a modification of the first embodiment of an exemplary window assembly 200. As shown in FIG. 2B, the arrangement of the window 212 is substantially similar to that of FIG. 2A. A notable difference in FIG. 2B is that the window 212 is arranged directly inside the inner surface of the inner sheath 204 and flush with at the distal end of the inner sheath 204. The inner sheath 204 can be made of a lubricious medical-grade plastic material reinforced by a metal coil. In this case, at least the distal end of inner sheath 204 is stripped of the plastic material and the metal coil is exposed, so that the window is fixed to the inner surface exposed wire of the sheath 204, and the detection fibers 208a and 208b are bonded to the outer surface of the exposed wire, as explained in more detail below (see FIGS. 6A, 6B, 7A, and 7B). In FIG. 2B, the protective metal can 206 is not used. This window assembly design according to FIG. 2B allows for further minimization of the endoscope outer diameter (OD), while still ensuring that the reflected light 216 is confined to the inside of the sheath 204 and is prevented from advancing towards the detection fibers 208a and 208b. That is, the illumination light reflected from the surfaces of window 212 (reflected light 216) does not reach the detection fibers 208a and 208b. However, in the same manner as in FIG. 2A, by arranging the distal surface of window 212 flush with the distal end of the sheath 204 and flush with the distal ends of detection fibers 208a and 208b, the collection optical path between the collection fibers and the imaging plane (sample) is not interfered.

For endoscopes containing both an illumination component and a detection component within the imaging probe core, imaging noise is significantly reduced if the window assembly selectively covers only the illumination component and blocks reflected illumination light from advancing to the detection fibers. Detection fibers are fixed surrounding the can or sheath holding the window and are thus not exposed to the reflected illumination light bouncing off from the surfaces of the window. As a result, imaging quality is improved by having suppressed (or at least reduced) the noise and cross-talk which is conventionally caused by the reflected light from the window.

Figure 3A:
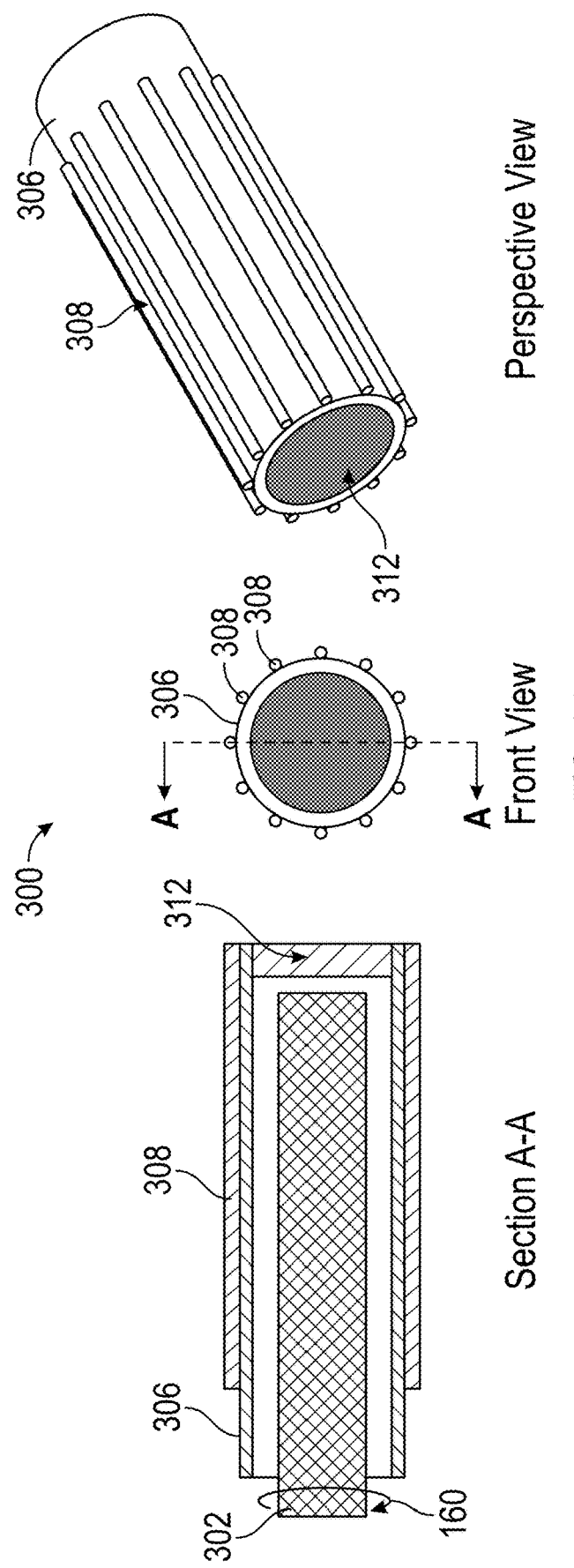

FIG. 3A and FIG. 3B show exemplary arrangements of a window and illumination fibers arranged at the distal end of the endoscope, according to the present disclosure. FIG. 3A shows a distal-end or front view (center), a perspective view (right side) and a cross-sectional view (left side) of an exemplary window assembly 300. According to the embodiment shown in FIG. 3A, a rotatable drive cable 302 (which contains thereinside the illumination fiber 201 and distal optics 203) is arranged concentric to a metallic can 306. In this embodiment, a window 312 protects the distal optics from the outside environment. The window 312 is arranged in the inner surface of the metallic can 306 and covers only illumination optics contained inside the can 306. A plurality of detection fibers 308 are bonded to the can 306 on the outer surface thereof.

FIG. 3B similarly shows a distal-end or front view (center), a perspective view (right side) and a cross-sectional view (left side) of an exemplary window assembly 300. FIG. 3B is structurally similar to FIG. 3A, except that FIG. 3B shows an outer protective layer 310 arranged concentric to the metallic can 306. As shown in FIG. 3B, the perspective view particularly shows the detection fibers 308 are arranged radially between the metal can 306 and the outer protective layer 310. The outer protective layer 310 serves to protect the detection fibers 308 from being exposed to the environment, and functions as a sterile cover. The outer protective layer 310 may be made of medical grade plastic material using a process previously disclosed by the applicant, for example, as described in publication US 2017/0290492 A1, which publication is herein incorporated by reference in its entirety. Plastic sheaths made of heat shrink, a bonded plastic sleeve, or dipped or spray coating of elastomeric material can be used to create the outer protective layer 310. The outer protective layer 310 may also be made of medical grade metal in the shape of a tubular shaft having an inner diameter fit to tightly enclose the detection fibers 308. Metal sheaths of a thin wall metal tube can be made using medical grade metals, such as stainless steel, cobalt, titanium, or alloys thereof.

In the embodiments shown in FIG. 3A and FIG. 3B, reflection of illumination light towards detection fibers 308 is eliminated or at least substantially reduced since the reflected light from the window is confined within the can 306 and/or the inner surface of outer protective layer 310. Therefore any stray light from the illumination beam is shielded from entering any detection fiber 308. This reduces the number of image artifacts and reduces imaging errors.

Detection fibers 308 are bonded and fixed to the outer surface of the can 306 and covered by the outer protective layer 310. The detection fibers 308 are bonded by applying an epoxy or adhesive or by dipped/spray encapsulation. Detection fibers bonded to the outer surface of a metallic can 306 will have a stronger bond compared to bonding to the inner sheath. In FIG. 3A, an inner sheath can be provided between the rotatable drive cable 302 and the metallic can 306 (similar to the arrangement of FIG. 2A). In that case, the inner sheath material can be low energy plastic material to promote low frictional forces of the spinning imaging core.

FIGS. 4A-4E illustrate specific designs of the window assembly and various processes by which the window may be attached to the distal end of the metallic can or sheath. Standard endoscopes use a metallic can with a window to encapsulate the entirety of the distal optics, including both illumination and detection fibers. In contrast, according to the present disclosure, the window arrangement is structurally different from the known technique in that the window is arranged to cover only the illumination components inside the can, whereas the detection fibers are fixed on the outer surface of the metallic can. This novel arrangement effectively prevents stray illumination light from being collected by the detection fibers.

In the present disclosure, for all distal end designs, the window is fixed to the metallic cylinder (metal can) by any joining process, such as soldering, brazing, thermal fusing, compression sealing, laser welding, or alternatively by a particularly strong (but light weight) adhesive. Thermal fusing chemically fuses materials together, whereas compression sealing creates a seal by mechanical compression without using any foreign sealing materials. A typical compression seal is to thermally expand a metal housing with a very precisely machined ID and place a cool sapphire or fused-silica glass window with equally precise OD into the metal housing ID. Once the two materials have achieved temperature equilibrium the window is hermetically sealed into the metal housing.

A window assembled into the distal end of a metal tube or metallic cylinder may have various designs as shown in FIG. 4A-4E. FIG. 4A shows a thru-hole design. A thru-hole (also "through hole" or "clearance hole") refers to a hole that is machined (reamed, drilled, milled, etc.) completely through the material on an object. Thru-hole technology also refers to a mounting technique used for building electronic components which involves the use of leads (wires) inserted through holes machined in printed circuit boards and soldered to terminal pads on the opposite side on an electronic component. In FIG. 4A, a window assembly "thru-hole" design refers to the arrangement of a transparent window 412 at the distal end of a metal tube 410 in a manner that the window 412 loosely slides into the inner circumference of the metal tube 410 and thereafter the window is rigidly fixed to the metal tube by either laser welding or adhesive bonding. Here, for the window 412 to loosely slide into the inner circumference of the metal tube 410, a certain degree of tolerance is necessary between the dimensions of the two mechanical elements.

Specifically, as shown in FIG. 4A, a circular window 412 of outer diameter (OD) within a minimum tolerance (e.g., within a few microns) of the inner diameter (ID) of a metal tube 410 is inserted and fixed with adhesive material or laser welded to an inner surface 413 at the distal end of a metal tube 410. Since the window 412 can be easily pushed through the ID of metal tube 410, this assembly method is the simplest design, which can be very economic in terms of cost, and rapid assembly. Advantages of a thru-hole design include fast assembly, low cost, simple design. However, if this window is used in a high-speed rotating probe, the window may be prone to dislodging (e.g., may pop out) from the inner surface 413 if the welding or bonding are not sufficiently strong. Therefore, this window arrangement could be better applicable to non-rotating or slow rotating probes. In addition, after the window is assembled inside the distal end of the metal tube, there are no mechanical features to maintain the alignment of the window to the endface of the probe. In this case, even if the surface of the window is aligned to be parallel to illumination core endface, the window may get misaligned with time, and errors in the coupling of the illumination light may occur. Therefore, a process of compression sealing can be used to more precisely secure the window 412 to the ID of metal tube 410.

FIG. 4B shows a slotted design in which the window 412 forms a joint 414 with the metal tube 410. As shown in FIG. 4B, the inner diameter of the metal tube 410 has a section at the distal end thereof with a wider inner diameter which serves as a counter bore. A window 412 with OD large enough to sit in the counter bored section is fitted and fixed tightly against the counter bore. If the metal tube 410 is made of a soft (malleable) metal material (e.g., brass), the distal end of the tube can be 'rolled' or "pushed" back to fold the end edge of the tube inward to form a sitting surface (counter bore) for the window 412. Advantageously, according to FIG. 4B, the window 412 has more surface area (the sitting surface of the counter bore and the inner surface of the tube) to bond to. In this manner, the window can be more precisely aligned with inner bore surface and with the endface of the optical probe. Since the counter bore reduces the wall thickness and may weaken the end structure of the tube, the metal tube 410 should have larger wall thickness than that of FIG. 4A.

FIG. 4C and FIG. 4D illustrate a "rolled" assembly design. In both cases where the window 412 is assembled into the distal end of the metal tube 410, the metal tube is preferably made of low hardness metal (e.g., brass). In the case of FIG. 4C, the metal tube 410 is placed in a fixture (pressure tool) that rolls the edge at the distal end thereof to embed or mechanically fix (fuse) the window within the inner cylindrical surface of the tube. This can be accomplished by applying a certain amount of pressure directly on the window 412, and slowly and evenly displacing the window 412 along the inner surface 413 of the metal tube 410. This process of inserting the window 412 by applying pressure causes the window 412 to form a lip or notch 415, whereby the window 412 remains securely fixed and accurately aligned with the metal tube 41o. In the case shown in FIG. 4D, the window 412 can be inserted first, and the distal edge of the metal tube 410 can then be rolled or folded inward to secure the window in place with a rolled lip 416. The rolled lip 416 will prevent the window 412 from popping out during high speed rotation. An advantage of the rolled design shown in FIG. 4C and FIG. 4D is that the window 412 is less prone to dislodging from its position due to force applied from drive cable core. For the "rolled" design shown in FIG. 4C and FIG. 4D, a soft metal material (e.g., brass) is preferred to be able to roll the material in a direction towards the proximal end. However, careful attention and high precision will be required as the rolled edges (if excessively large) could block some of the illumination light from exiting towards the sample.

FIG. 4E shows another exemplary window assembly design called "bored from proximal end". According to FIG. 4E, the metal tube 410 is bored from the proximal end leaving a lip or notch 417 at the distal end of the tube, which provides a precise and large surface area for the window 412 to sit on. According to this embodiment, the inner diameter of the metal tube 410 is bored slightly larger (within a few microns tolerance) than the outer diameter of the window 412. In this case, the window 412 is loosely inserted from the proximal end of the metal tube 410, and is then fixed by either laser welding or a strong adhesive. Alternatively, when lip or notch 417 is strong enough to withstand certain amount of pressure, the window 412 can be pressured in the direction from the proximal to the distal end, for example, by the endface of the optical probe abutting against the surface of the window. An advantage of this assembly design is that the window 412 would be less prone to mechanical failure. That is, the lip or notch 417 would prevent the window 412 from dislodging or moving due to force applied from drive cable core. In addition, by securing the window 412 between the endface of the optical probe and the lip 417, the window 412 can be more accurately aligned with the distal optics of the probe. However, since the window 412 has to be assembled from proximal end with certain amount of diameter tolerance, the fixation of the outer edge of the window 412 to the inner surface 413 of the metal tube 410 can be challenging. For example, if epoxy is used for fixation, attention should be paid that epoxy does not get on the faces of the window. If the metal tube 410 has a long bore section, accurate assembly would take more time. Therefore, the "bored from proximal end" design would limit the length of the tube itself, and would be better applicable to endoscopes having relatively short probes.

<Grooved can Window Assembly>

Figure 5:
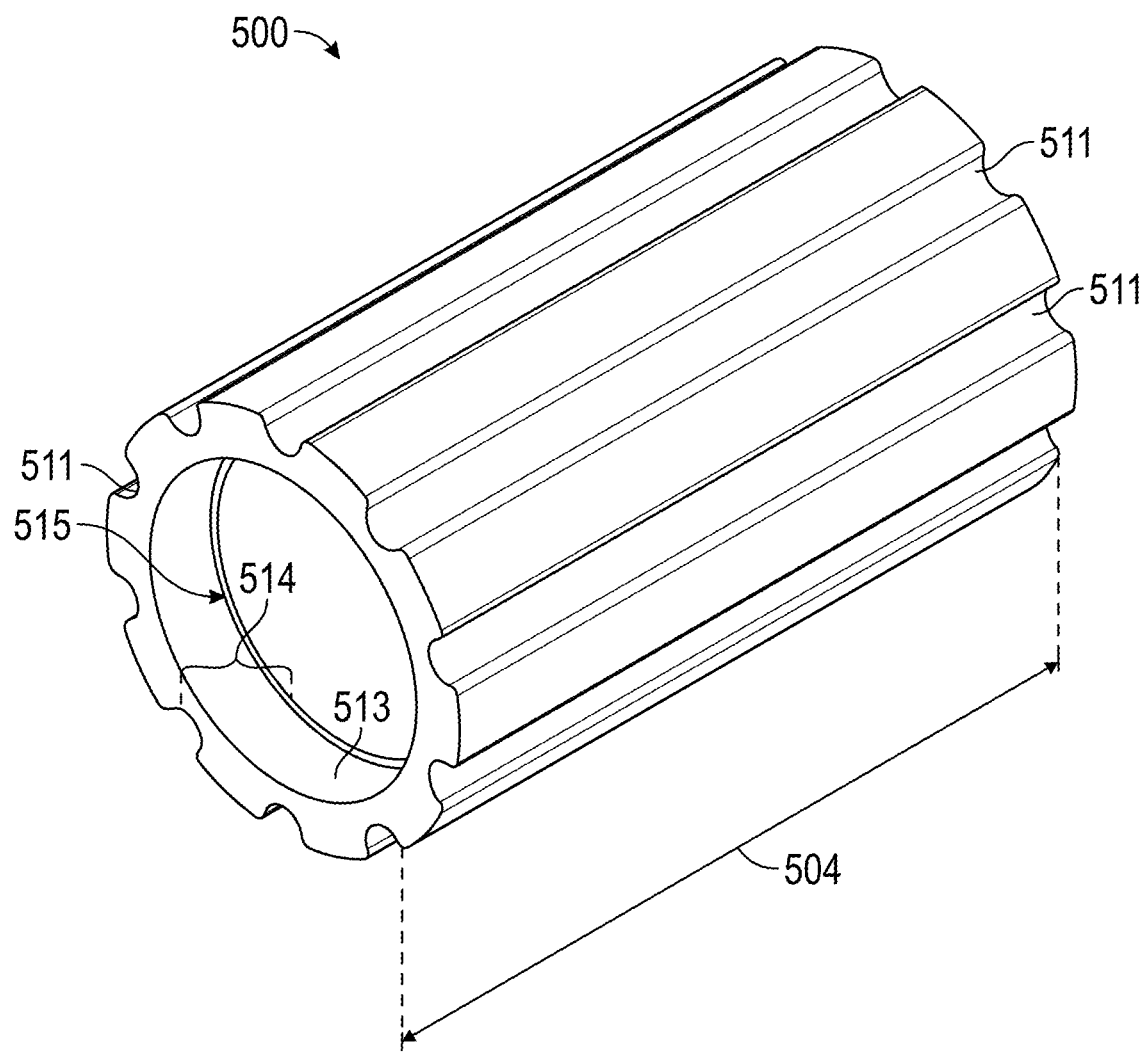
FIG. 5 illustrates an exemplary Grooved Can design.

FIG. 5 illustrates a Grooved Can design 500. As shown in FIG. 5, the grooved can design 500 includes a tubular shaft 504 having a cylindrical outer surface machined or etched with groves 511 and a cylindrical inner surface machined or etched with a notched section 514. The grooves 511 are so configured and dimensioned for receiving therein detection fibers (not shown), and the notched section 514 in the inner surface is so configured and dimensioned to receive therein a window (not shown). Since the grooves can be machined with high precision and specific sizes, the detection fibers can be arranged to sit on grooves 511 for precise alignment and fixation. The tubular shaft 504 includes at the distal end thereof a portion of its inner diameter bored to form a notch 515 and a seating surface 513 to receive the window. In some embodiments, the tubular shaft 504 may be a metallic tube made of medical-grade metal or metal alloys (e.g., stainless steel, cobalt-based alloys, titanium or titanium alloys), and the grooves 511 can be machined or etched on the outer surface of the metallic tube. In some embodiments, the tubular shaft 504 may be a plastic tube made of medical-grade sturdy plastic, and the grooves 511 can be machined or etched on the outer surface of the plastic tube. In some embodiments, in particular when using medical-grade plastic materials, the grooves 511 may be formed, by a process of additive manufacturing (3D printing) in which material is joined or solidified layer-by-layer under computer control to create the entire tubular shaft 504 with the notch 515 and seating surface 513 with the desired dimensions and shape.

Advantageously, in a grooved can design 500, grooves can be machined to specific dimensions according to the number and size of applicable fibers, so as to allow for better alignment and fixation of the detection fibers to the outer surface of the can. Grooves can allow for greater bonding surface for adhesives or coatings to more firmly fix the detection fibers to the probe, so as to avoid dislodging during high-speed rotation. It should be noted, however, that for machining the grooves 511 on the tubular shaft 504, a larger wall thickness and thus greater outer diameter may be required to create these features. Therefore, a thin walled tube with a small diameter may not be applicable for this process. Nevertheless, since the grooves and window seating surface can be manufactured to desired shape and specification, grooved can assembly can be advantageous in facilitating easy assembly and more accurate alignment of both the window and detection fibers.

<Sheath Coil Window Assembly>

In spectrally encoded endoscopy (SEE) applications, the imaging probe uses an inner sheath which houses the spinning illumination core. In this case, the inner sheath houses a rotating drive cable (or torque wire coil) that is the illumination core. A flexible drive cable serves to transmit a rotational torque from a motor located at the proximal end of the probe to the distal optics located in the distal end thereof. In addition to rotation, the flexible drive cable also serves to implement linear translation of distal optics within the bodily lumen where the endoscope or catheter is used, by pushing or pulling on the proximal end of the drive cable. Therefore, the need to transmit rotational torque and to provide linear translation requires the drive cable to have certain stiffness to prevent the tubular shaft from being deformed or crushed.

In applications where a flexible endoscope (or catheter) is required, the inner sheath itself is designed with an embedded wire or coil. The inner sheath is embedded with wires or a braid that reinforces the sheath and keeps it circular and prevents crushing or kinking while bending. These wires or braid are fixed within the sheath. Prevention of 'ovalization' or kinking of the sheath while operating the rotating drive cable thereinside is critical to reduce friction. Flat wires embedded within the sheath are particularly useful for providing crush resistance and for keeping the central cylindrical space round during bending, which is an important attribute for imaging catheters and endoscopes that require a rotating imaging element enclosed within a sheath. Flat wires embedded within the inner surface and the outer surface of the sheath provide minimal wall thickness to the sheath to minimize the overall outer diameter. In particular, in the case of adding a window to the distal end of the inner sheath, flat wires embedded in the sheath wall can be more effective than round wires for attaching to the outer diameter of the window. However, other wire shapes may alternatively be used, such as round, oval, square wires and the like. The coiling of the flat wire may be a tight coil or it may be loosely coiled depending on the level of stiffness desired for the inner sheath.

Since the spinning core rotates at high speeds and it is desirable to prevent or minimize non-uniform rotational distortion, the inner sheath needs to have low friction coefficient. Therefore, plastic materials with low friction properties, such as polyimide (PI), Fluorinated ethylene propylene (FEP), Teflon® made of polytetrafluoroethylene (PTFE), or similar materials, are used for the tubular inner sheath. However, the material properties of such plastics make the surfaces of the inner sheath nearly un-bondable to other materials via standard adhesives.

As noted above, if the endoscopic window is fixed directly inside the inner diameter of the inner sheath, it is possible to eliminate the use of the metal can component at the distal end of the probe, and this minimizes the overall outer diameter of the scope. However, since the plastic of the inner sheath does not bond well with most adhesives, it is necessary to find alternative solutions. Therefore, according to an embodiment of the present disclosure, a window at the distal end of the spinning core is configured to be fixed to exposed metal material (wire) of an embedded coil of the inner sheath.

Figure 6A:
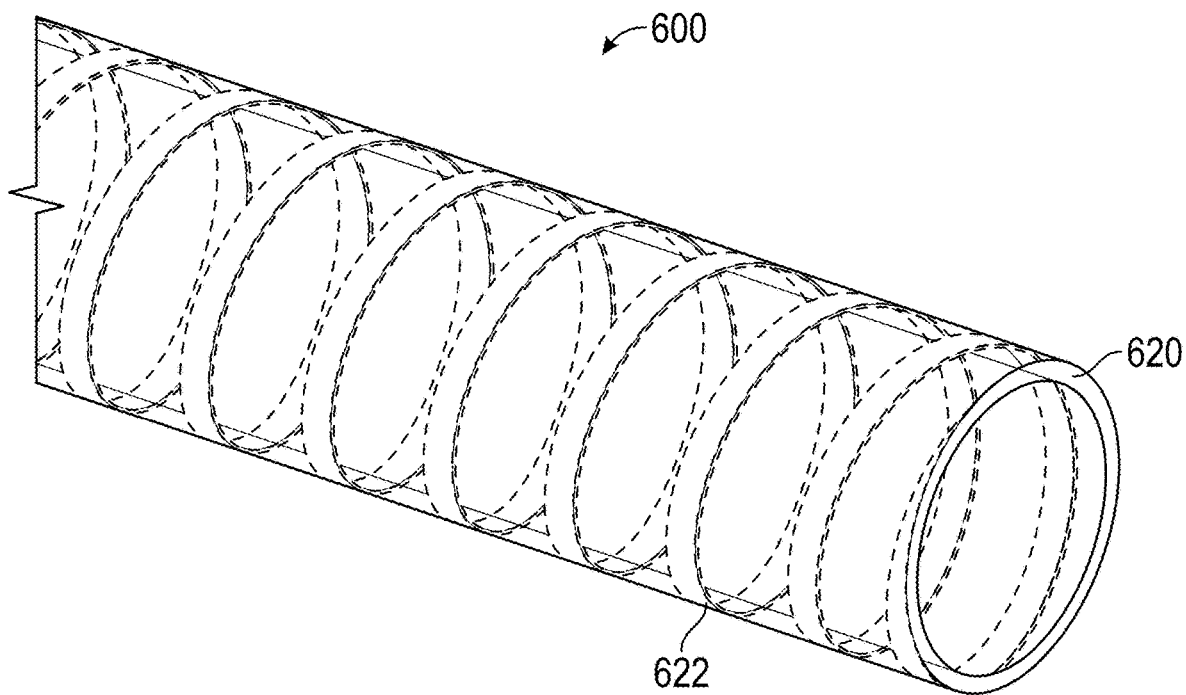
FIGS. 6A and 6B show an example of a flexible sheath having a wire coil embedded therein.
Figure 6B:
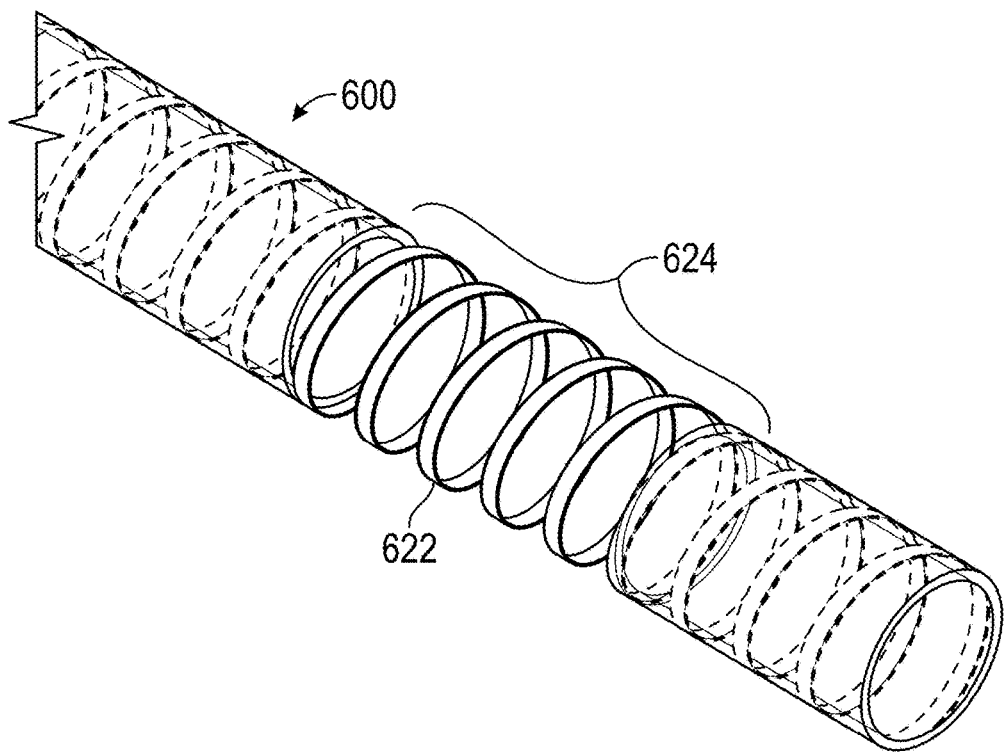

FIG. 6A and FIG. 6B show an example of a sheath 600. The sheath 600 includes a tubular shaft 620 and a wire coil 622 embedded within the wall of the tubular shaft. The tubular shaft 620 is preferably a plastic tube made of medical-grade elastomeric or plastic materials, and the wire coil 622 is a wire made of metal materials, such as stainless steel, wound into a long and flexible sequence of joined circles or rings twisted to form a hallow tube. In an inner sheath having the structure shown in FIG. 6A, the wire of coil 622 is exposed by melting or stripping a section 624 of the inner sheath to remove the plastic material surrounding the wire. The plastic material of section 624 can be removed by other methods too, such as laser ablation or chemical dissolving, so as to leave the wire coil 622 exposed.

In this manner, after the plastic material is removed, the window can be inserted into the inner diameter of the sheath, and then be fixed to the inner diameter of the coil 622. The window can be fixed to the wire coil 622 by laser welding or adhesive bonding.

Figures 7A, 7B:
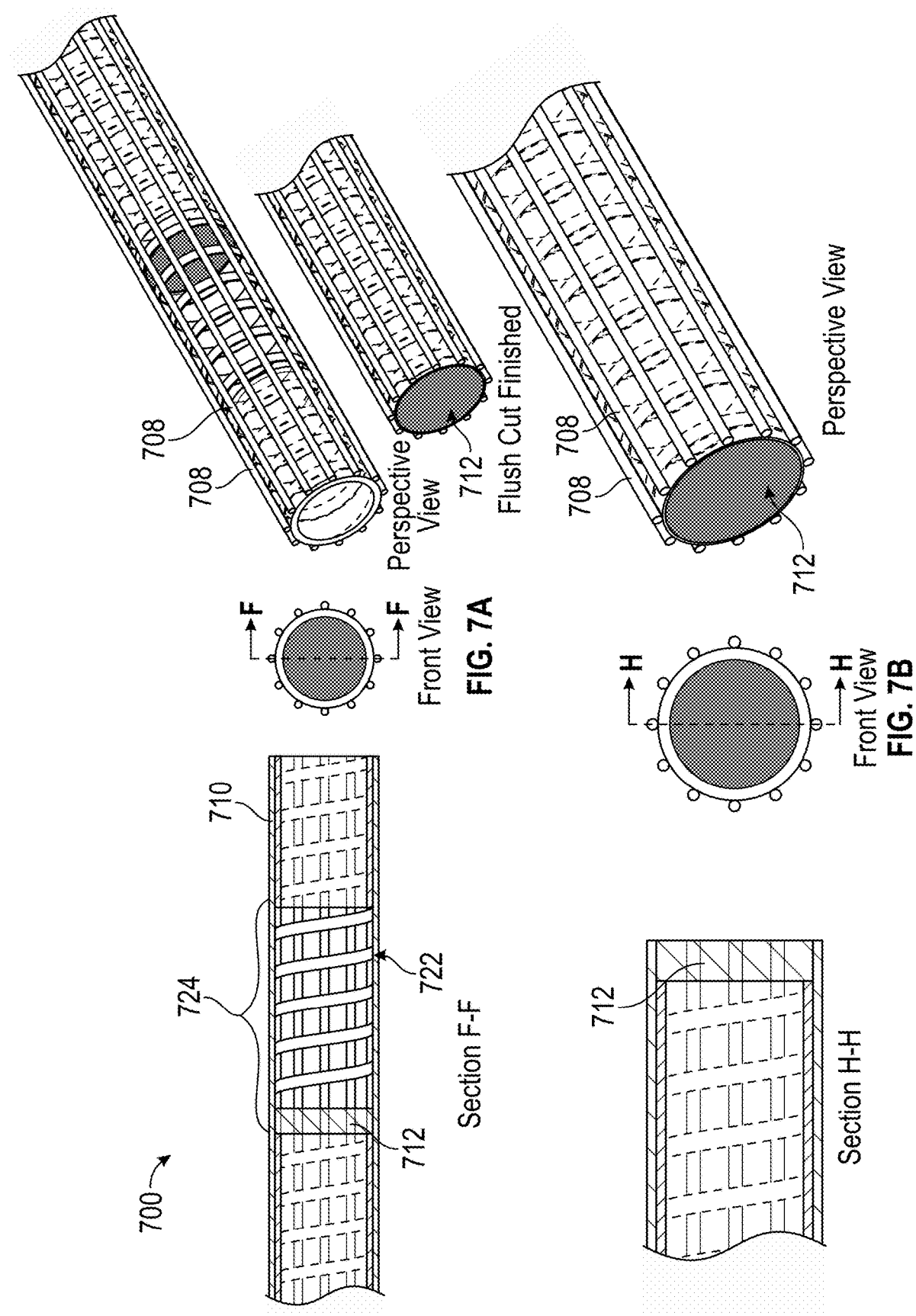
FIG. 7A shows an embodiment of a window assembly 700, where a window is arranged inside (in the inner diameter) of a section of sheath where the wire coil has been exposed, and detection fibers are arranged on the outer surface of the sheath.
FIG. 7B shows an embodiment of a window assembly 700, where a window 712 and detection fibers 708 are respectively fixed to the inner surface and outer surface of sheath 710 without exposing the coil wire 722.

FIG. 7A shows an embodiment of a window assembly 700. As shown in FIG. 7A, a window 712 is arranged inside (in the inner diameter) of an inner sheath 710. In FIG. 7A, a section 724 of the sheath has been exposed by removing the plastic material thereof and exposing a wire coil 722.

After the sheath is prepared in the manner described above with respect to FIGS. 6A and 6B, detection fibers 708 are aligned along the outer surface of the inner sheath 710 and are bonded to the exposed wire 722 at the distal end. The final assembly is cut at the edge of the window, and polished to create a flush surface for the distal end of the scope, as shown on FIG. 7A (flush cut finished).

Alternatively, as shown in FIG. 7B, the window 712 and detection fibers 708 can be fixed directly to the surface material of the sheath 710 with a special primer and adhesive material specifically designed to provide greater bonding strength with materials such as PI or PTFE. One example of a priming material to promote bonding to materials, such as PTFE and PI, is Loctite® SF 770 (known as Loctite 770) and commercially available from the Henkel Corporation.

The elastomeric plastic sheath, which does not usually bond well with conventional adhesives, can be coated or jacketed with another material that allows for better bonding. In this manner, the window 712 and detection fibers 708 can be fixed respectively to the inner surface and outer surface of sheath 710 without exposing the coil wire 722, as shown in FIG. 7B.

For example, in a sheath of pure PTFE material, the sheath allows for low-friction spinning of the imaging core, however the detection fibers cannot be securely bonded to the outer surface. In this case, selection of a pure PTFE sheath lined with polyurethane (PU) coating allows for a sheath with low-friction inner surface of PTFE with bondable outer surface of PU. The PTFE liner is coated with PU to form the outer coating. In the case of sheaths with embedded wires or braid, the liner is wrapped with a wire coil/braid then coated with the outer material to lock the wires to the liner. Detecting fibers can be bonded to exposed coil or to an outer surface of bondable material, so that the detection fibers are less likely to become dislodged during high-speed spinning.

<Detection Fiber Assembly>

Detection fiber selection and arrangement is an important aspect in assembling an endoscopic window. The number of detection fibers to be arranged on the outer diameter of inner sheath in the SEE scope is determined by the optical requirements of the application. A minimum of one (1) detection fiber is needed to collect light from a sample to form an image. More detection fibers increase the amount of light collected and create a higher quality image. More detection fibers also increase the assembly time, and increase the difficulty in handling, aligning, cutting, and polishing. An increased number of detecting fibers also increases the amount of material and assembly costs. Diameter: Larger diameter fibers can collect more light, but this increases the overall outer diameter of the scope. In contrast, small diameter fibers are more delicate and harder to handle. In one embodiment, detection fibers for the SEE scope may range from 30 μm to 120 μm in diameter.

Fiber arrangement: In a SEE endoscope it is desirable to arrange detection fibers evenly spaced around a circumference at the distal end of the inner sheath or of the metallic can to allow for even collection of light. To facilitate even (parallel) arrangement, spacers of similar diameter to the detection fiber may be used to allow for better distribution alignment of the fibers around the distal end of inner sheath or metallic can. Spacers may be created by non-functional fibers, plastic or glass rods, or metal wire arranged parallel to the one or more detection fibers.

To optimize the collection of light it is desirable to arrange the detection fibers around a full annular ring. The full circumference around the distal end of the inner sheath or metallic can is preferably packed with functional detection fibers. The maximum number of fibers is determined by the OD of the sheath/can and the OD of the detection fibers. In some embodiments, a multilayer arrangement may be desirable. Multiple layered annular rings of detection fibers can be incorporated in the design according to the desired application. Naturally, it should be kept in mind that the increase in detection fibers increases the collection efficiency of imaging light, but at the same time, each layer of fiber will increase the overall OD of the scope. In addition to optimal fiber arrangement, the window can be coated with anti-reflective coating to reduce backscatter from any possible stray illumination light.

<Exemplary Assembly Process>

An exemplary Window Assembly process includes the following steps:

Step 1: Prepare the inner diameter of the metallic can or inner sheath. In some embodiments, the inner diameter of a metallic tube may be prepared using a mandrel to form the metallic can according any of the shapes illustrated in FIGS. 4A through 4E. In one embodiment, the distal end of an appropriately sized mandrel may be equipped with a precision cutting tool (e.g., a lathe) to form the receiving surface for the window. In other embodiments, preparing the inner diameter of the sheath includes exposing the coil wire by removing the plastic material from the sheath, as shown in FIGS. 6A-6B.

Step 2. Insert window through the inner diameter of the metallic can or inner sheath. When the endoscope includes the metallic can, the window can be inserted as explained above according to each of the designs of FIGS. 4A-4E. When the metallic can is obviated, and the window is to be fixed to the exposed coil wire, the window could be mounted to the distal end of an appropriately sized mandrel and driven to the desired position inside the inner diameter of the sheath as shown in FIG. 7A. When the window is fixed directly on the plastic surface of the sheath, as shown in FIG. 7B, the window may be mounted by small mechanical tools or even by hand. In particular, when the window is assembled at the distal end of a grooved can, as shown in FIG. 5, the receiving surface 513 and notch 515 are used as a guide to precisely center and align the window with the grooved can 504.

Step 3. Fix the window to the inner diameter of the metallic can or inner sheath. As described above, the window can be laser welded or attached by adhesive bonding. In one embodiment, polymer bonding may be preferred. The boding step may be performed by a dip casting process. The above tube-wire assembly is coated by dipping into a first polymer solution, which is a low-viscosity solvent carrying a polymer. This can be done to lock the window to the metallic can or to coiled wires. The dip casting can also form an adhesive layer on the outer surface of the metallic can or sheath onto which the detection fibers can be attached. The polymer used for the dip casting can be, for example, polyurethane, silicone, butadiene-styrene, styrene-ethylene, polyvinyl chloride, polyethylene, and mixtures of these. The polymer thus can form a translucent thin film around the edges and the endface of the window and therefore helps seal the distal optics from the outside environment.

Step 4: Place at least one detection fiber along the outer surface of the metallic can or inner sheath. In this step, one or more optical fibers such as detection fibers 308 or 708 are arranged around the distal end of the metallic can or inner sheath. In addition to the detection fibers, as describe above, spacers of similar diameter to the detection fibers may be arranged to allow for better distribution alignment of the fibers around the distal end of inner sheath or metallic can. Spacers may be created by non-functional fibers, plastic or glass rods, or metal wire arranged parallel to the one or more detection fibers. In some embodiments, any number between 1 and 36 optical fibers (e.g., 2, 4, 6, 8, 10, 15, 16, 20, 24, or more) are placed concentrically around the assembly to create a ring of detection fibers. In some embodiments, placing the fibers means rolling the assembly over an array of fibers that are touching or particularly spaced apart. In some embodiments, the thin layer of polymer coating is sufficiently adhesive to hold the at least one optical fiber in place during a second dipping process. In other embodiments, fibers are inserted along grooves as those shown in FIG. 5.

FIGS. 8A-8F show various examples of the manner in which detecting fibers 808 can be arranged concentrically around the distal end of the metallic can or inner sheath 810. In FIG. 8A, a single detecting fiber 808 is arranged on the outer surface of sheath 810, such that the end-surface (endface) of a window 812 is flush with the distal end surface of the sheath 810 and flush with the tip of fiber 808. In FIG. 8B, three detection fibers 808 are arranged on the outer surface of sheath 810 concentrically around window 812. In FIG. 8C, a plurality of detection fibers 808 are arranged equidistantly on the outer surface of sheath 810 concentrically around window 812. In FIG. 8D, a plurality of detection fibers 808 and spacers 809 are arranged interposed between each other on the outer surface of sheath 810 concentrically around window 812. In FIG. 8D, each detection fiber 808 is arranged interposed by two spacers 809, but the arrangement can be such that only one spacer 809 or more than two spacers 809 are arranged between two consecutive detection fibers 808. In FIG. 8E, a plurality of detection fibers 808 are arranged on the outer surface of sheath 810 concentrically around window 812 such that the entire circumference filled by detection fibers without spacers therebetween. In FIG. 8F, multiple layered annular rings of detection fibers 808a and 808b are arranged on the outer surface of sheath 810 concentrically around window 812. In this arrangement, a first annular ring of fibers 808a and a second annular ring of fibers 808b are arranged radially with respect to window 812.

Step 5 (optionally). Dip the assembly including the at least one optical fiber into a second polymer solution to begin forming a second thin dip-cast polymer layer. This layer may form on and around the detection fibers 308 or 708 with or without spacers therebetween. The polymer used for the second dip-casting step (the second polymer solution) may be the same or different from the polymer of the first polymer solution, and may be provided at the same or different concentration. The second dip-cast polymer would result in a thin outer protective layer 310 as that shown in FIG. 3B.

Step 6. Remove any excess polymer solution from the distal end of the assembly and cut and/or polish any excess fiber material to form a flush finish to minimize optical aberrations. In this step, it may be necessary to use a solvent to flash off any excess polymer coating. The final assembly is cut and polished to create a flush surface for the distal end of the scope, as shown on FIG. 7A (flush cut finished).

<Window Forming>

There are various manners in which the window itself can be fabricated. In some embodiments, a window element can be formed from common, optically transparent materials such as glass, silica, sapphire, quartz, etc. In other embodiments, a cylinder of medical grade thermoplastic (e.g., PEBAX® (available from Arkema S.A.)) can be inserted into the inner diameter of the metal tube or sheath and machined in the manner described above in reference to FIGS. 7A and 7B.

Cored Slide Glass: In one embodiment, a window can be a piece of cored slide glass (a circular piece of glass cut from slide glass) fitted to the inner diameter of the sheath or metal tube. The process of cutting slide glass into circular pieces represents certain challenges because machining the delicate slide glass for the window may result in chipping or breakage. Special tools are necessary to handle extremely small parts (the diameter of the window can be as small as 1 mm or less, and the thickness is in the range of 100 or less microns). In addition, careful attention must be maintained during the bonding of the window to the inner diameter of the metal can or inner sheath as epoxy on optical faces of the window can be detrimental to imaging quality. To obviate the detriments of using epoxy adhesives, laser welding or ultrasonic welding of the thin window may be preferable. Cored slide glass may be referred to machine cut glass. However, class cutting, as commonly referred, is not really cutting. What actually takes place is a "score" or a fine shear on the glass surface to break the glass in a desired shape. The lighter the score, the better and more accurate the break-out. Carbide cutting wheels available from, for example, The Fletcher-Terry Company, LLC may be used to cut circular glass window.

Polished Glass Rod: In some embodiments to avoid the detriments of using cored slide glass, the window may be fabricated from a solid glass rod. In this case, a solid glass rod is fitted to the inner diameter of the metallic can or inner sheath and is bonded therein using adhesives. Then, the glass-rod and metal can (or glass-rod and sheath) assembly is cut and polished down to the desired dimensions. In this case, aspects to be considered include the possible waste of material, which would increase the final cost of the scope, and the need for high accuracy to control the glass rod thickness to form a window having a thickness in a range of 100-200 µm. The window diameter can range between 0.3-1.0 mm.

Integrally formed: In some embodiments, the window may be integrally formed with the sheath by using one or more layers of optically transparent polymeric material as described in applicant's previously disclosed publication US 2017/0290492 A1, which is incorporated by reference herein in its entirety.

According to the present disclosure, the window is designed to cover only the illumination optics of the scope, therefore preventing the detection fiber(s) from being exposed to reflected illumination light. In some embodiments, the window is bonded within the inner sheath as opposed to a metal can. In this case, it is possible to have smaller overall scope diameter. One or more detection fibers are bonded to the outer surface of the sheath (or metal can) encapsulating the illumination optics. In this manner, it is less likely that detection fibers would slip or become detached during stretching or bending of the scope.

<Other Assembly Options>

As it will be understood by persons having ordinary skill in the art, the manner in which the window and detection fibers are assembled with the metal can or inner sheath is not limited to the exemplary processes described above. Several other processes are available and would be applicable and adaptable to forming the window assembly disclosed herein. In that regard, at least the following assembly options can be applicable:

Epoxy Assembly

An epoxy assembly process includes the following steps:

STEP 1: Glue window to endface or inner diameter (ID) of metal tube (can) with appropriate epoxy bonding material.

STEP 2: Assemble detection fibers around circumference of metal can and fix the detection fibers to outer surface of metal tube with epoxy.

STEP 3: Apply outer coating or sheath jacket to assembly (sheath, heatshrink, dip/spray coat, etc.)

STEP 4: Remove excessive material from distal endface of assembly to ensure that window and fibers are polished flat and flush with distal end of metal tube.

Laser and Epoxy Assembly

A process of using laser and epoxy for assembling the window and detecting fibers with the metal tube is similar to the process for Epoxy assembly. However, the step of attaching the window to the endface of the metal tube is preferably done by laser welding because laser welding has certain advantages over the use of epoxy materials. One advantage of laser welding is that, in contrast to gluing or bonding, no additional materials that could be susceptible to evaporation or embrittlement are required. This means reduced costs and increases the durability and stability of the seam. Therefore, in a laser and epoxy assembly process the following steps are contemplated.

First: a window is laser welded to the endface or ID of the metal can.

Second: Detection fibers are assembled around the outer surface of the metal can and fixed therein with epoxy.

Third: An outer coating or sheath jacket is applied to the assembly (sheath, heatshrink, dip/spray coat, etc.).

Fourth: The distal endface of the metal tube is polished flat with window and fibers remaining flush with the distal endface of the metal tube.

Laser Weld Assembly

First: Within the laser welding equipment, fixture+align the window (cored slide glass or glass rod) to the metal can and arrange the detection fibers to the outer surface of the metal can.

Second: Laser weld the distal end of the metal can thereby fusing the window to the endface of the metal can.

Third: Laser weld the detection fibers fusing the detection fibers to each other as well as to the surface of the can.

Fourth: Apply outer coating or sheath jacket to assembly (sheath, heatshrink, dip/spray coat, etc.)

Fifth: Polish (a) distal face (endface) of metal can, (b) window, and (c) distal ends of detection fibers.

Ultrasonic Weld Assembly

Ultrasonic welding (USW) is an industrial welding technique whereby high-frequency ultrasonic acoustic vibrations are locally applied to workpieces being held together under pressure to create a solid-state weld. It is commonly used for plastics, and especially for joining dissimilar materials; thin metals can also be welded with USW. In ultrasonic welding, there are no connective soldering materials necessary to bind the materials together. In the medical industry ultrasonic welding is often used because it does not introduce contaminants or degradation into the weld, and does not interfere with the biocompatibility of welded parts. This prevents contamination and reduces the risk of infection. The method of assembling a transparent (glass) window and detecting fibers with a metal tube (metal can) contemplated in the present disclosure, as illustrated in FIGS. 3A, 3B, and 4A-4E, can utilize the ultrasonic welding techniques such as is described in U.S. Pat. No. 3,563,822 to Fesh and U.S. Pat. No. 3,224,916 to Soloff et al., for example.

In the ultrasonic welding process, according to the present disclosure, the following steps are contemplated:

First: within the ultrasonic welding equipment, fixture+align the window (cored slide glass or glass rod) to the metal can and the detection fibers to the circumference of the metal can.

Second: apply ultrasonic weld to the distal end of the metal can to fuse the window to the endface of the metal can.

Third: ultrasonically weld the detection fibers fusing at least the distal ends of the detection fibers to each other as well as to the outer surface of the metal can.

Fourth: apply outer coating or a sheath jacket to the assembly (sheath, heatshrink, dip/spray coat, etc.)

Fifth: Polish the distal end of metal tube to make if flush with the window and fiber ends.

Definitions

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. An endoscopic probe, comprising:
    a tubular shaft having a cylindrical passage extending from a proximal end to a distal end along a central longitudinal axis;
    first optics arranged along the cylindrical passage and configured to rotate around the central longitudinal axis inside the tubular shaft;
    second optics arranged to at least partially surround the distal end of the tubular shaft; and
    a window having substantially parallel proximal and distal surfaces arranged at the distal end of the tubular shaft,
    wherein the first optics includes rotatable illumination optics configured to guide illumination light towards a sample, and the second optics includes detection optics configured to collect light reflected, scattered, and/or emitted from the sample,
    wherein the window is arranged to cover and seal the rotatable illumination optics inside the tubular shaft so as to prevent a reflected illumination light reflected from one or more of the proximal and distal surfaces of the window from reaching the detection optics,
    wherein the tubular shaft includes a cylindrical sheath made of elastomeric material with a metallic wire embedded between an inner surface and an outer surface of the cylindrical sheath, and
    wherein the window is mechanically attached to a section of the metallic wire of the cylindrical sheath from which the elastomeric material has been removed.

2. The endoscopic probe according to claim 1,
    wherein the rotatable illumination optics is configured to guide the illumination light through the window towards the sample.

3. The endoscopic probe according to claim 2, wherein the detection optics includes at least one detection optical fiber arranged on an outer surface of the tubular shaft, wherein the rotatable illumination optics is arranged within a rotatable drive cable which is concentric with the tubular shaft, and wherein the window seals the rotatable drive cable and the rotatable illumination optics inside the cylindrical passage without interfering with an optical path of the at least one detection optical fiber such that the illumination light guided by the rotatable illumination optics and partially reflected on the one of more of the proximal and distal surfaces of the window does not reach a distal end of the at least one detection optical fiber.

4. The endoscopic probe according to claim 2, wherein the rotatable illumination optics includes an optical fiber and distal optics which rotate inside the tubular shaft, wherein the tubular shaft includes the metallic wire which is cylindrically coiled and embedded between the inner surface and the outer surface of the cylindrical sheath, and wherein the window includes a circular piece of transparent material configured to fit in an inner diameter of the cylindrically coiled metallic wire.

5. The endoscopic probe according to claim 4, wherein the window has a diameter in a range of 0.3 to 2 mm and a thickness in a range of 100 to 200 microns, and wherein the window is rigidly fixed to an inner surface of the cylindrically coiled metallic wire, at the distal end thereof, by one or more of laser welding, ultrasonic welding, or adhesive bonding.

6. The endoscopic probe according to claim 1, wherein the metallic wire is a flat wire, or a round wire, or an oval wire, or a square wire which is coiled or braided within the elastomeric material of the cylindrical sheath, and wherein the window is joined, by either laser welding or ultrasonic welding or bonding with an adhesive material, to the section of the metallic wire of the cylindrical sheath from which the elastomeric material has been removed.

7. The endoscopic probe according to claim 2,
    wherein the detection optics includes a plurality of detection optical fibers,
    wherein the cylindrical sheath includes a plurality of grooves formed on the outer surface thereof, and
    wherein each groove of the plurality of grooves extends substantially parallel to the central longitudinal axis of the tubular shaft and is configured to receive therein at least one of the plurality of detection optical fibers.

8. The endoscopic probe according to claim 2, wherein the detection optics includes a plurality of detection optical fibers, wherein the plurality of detection optical fibers are joined, by either laser welding or ultrasonic welding or bonding with an adhesive material, to an outer surface of the tubular shaft, such that distal ends of the plurality of detection optical fibers are flush with the distal end of the tubular shaft and flush with the distal surface of the window, and wherein the rotatable illumination optics includes an illumination optical fiber, a focusing element, and a diffracting element arranged within a rotatable drive cable with rotates with respect to the tubular shaft.

9. The endoscopic probe according to claim 1,
    wherein the window is a circular window made of optically transparent material selected from glass, silica, sapphire, quartz, or medical grade thermoplastic, and
    wherein the window is arranged inside the cylindrical passage at the distal end of the tubular shaft such that the window is perpendicular to the central longitudinal axis.

10. A method of assembling an endoscopic probe, comprising:
    arranging first optics inside a tubular shaft which has a cylindrical passage extending from a proximal end to a distal end along a central longitudinal axis;
    arranging second optics so as to at least partially surround the distal end of the tubular shaft; and
    arranging at the distal end of the tubular shaft a window having substantially parallel proximal and distal surfaces, wherein the first optics are configured to rotate around the central longitudinal axis inside the cylindrical passage, wherein the first optics includes rotatable illumination optics configured to guide illumination light towards a sample, and the second optics includes detection optics configured to collect light reflected, scattered, and/or emitted from the sample, wherein the window is arranged to cover and seal the rotatable illumination optics arranged inside the cylindrical passage so as to prevent a reflected illumination light reflected from one or more of the proximal and distal surfaces of the window from reaching the detection optics, wherein the tubular shaft includes a cylindrical sheath made of elastomeric material with a metallic wire embedded between an inner surface and an outer surface of the cylindrical sheath, and wherein arranging the window at the distal end of the tubular shaft includes mechanically attaching the window to a section of the metallic wire of the cylindrical sheath from which the elastomeric material has been removed.

11. The method according to claim 10,
wherein arranging the first optics includes arranging the rotatable illumination optics inside the tubular shaft to guide through the window the illumination light towards the sample.

12. The method according to claim 11,
wherein arranging the detection optics includes arranging one or more detection optical fibers on an outer surface of the tubular shaft such that distal ends of the one or more detection optical fibers are flush with the distal end of the tubular shaft, wherein arranging the window includes sealing the rotatable illumination optics inside the cylindrical passage of the tubular shaft with the window, such that the distal surface of the window is flush with the distal end of the tubular shaft and flush with the distal ends of the one or more detection optical fibers, and wherein the window does not interfere with a light collection optical path of the one or more detection optical fibers.

13. The method according to claim 11, wherein arranging the rotatable illumination optics in the tubular shaft includes arranging the rotatable illumination optics inside a rotational drive cable which is configured to rotate relative to the tubular shaft, wherein the tubular shaft includes the metallic wire which is cylindrically coiled between the inner surface and the outer surface of the cylindrical sheath, and wherein arranging the window at the distal end of the tubular shaft includes arranging the window in an inner diameter off the cylindrically coiled metallic wire.

14. The method according to claim 13,
wherein arranging the rotatable illumination optics in the tubular shaft includes arranging an optical fiber and distal optics inside the rotational drive cable.

15. The method according to claim 10, wherein the metallic wire is a flat wire, or a round wire, or an oval wire, or a square wire which is coiled or braided within the elastomeric material of the cylindrical sheath, and wherein mechanically attaching the window includes joining the window, by either laser welding or ultrasonic welding or bonding with an adhesive material, to the section of the metallic wire of the cylindrical sheath from which the elastomeric material has been removed.

* * * * *